United States Patent
Tu et al.

(10) Patent No.: US 11,933,777 B1
(45) Date of Patent: Mar. 19, 2024

(54) MODEL FOR PREDICTING BIOAVAILABILITY OF ARSENIC IN SITE SOIL AND CONSTRUCTION METHOD AND APPLICATION THEREOF

(71) Applicant: Institute of Soil Science, Chinese Academy of Sciences, Nanjing (CN)

(72) Inventors: Chen Tu, Nanjing (CN); Yongming Luo, Nanjing (CN); Ying Liu, Nanjing (CN); Guoming Liu, Nanjing (CN); Shuai Yang, Nanjing (CN)

(73) Assignee: INSTITUTE OF SOIL SCIENCE, CHINESE ACADEMY OF SCIENCES, Nanjing (CN)

( * ) Notice: Subject to any disclaimer, the term of this patent is extended or adjusted under 35 U.S.C. 154(b) by 0 days.

(21) Appl. No.: 18/497,047

(22) Filed: Oct. 30, 2023

(30) Foreign Application Priority Data

Nov. 7, 2022 (CN) .......................... 202211382390.4

(51) Int. Cl.
  *G01N 33/24* (2006.01)
  *G06F 30/20* (2020.01)

(52) U.S. Cl.
  CPC ............. *G01N 33/24* (2013.01); *G06F 30/20* (2020.01); *G01N 2033/243* (2013.01)

(58) Field of Classification Search
  CPC ............................... G01N 33/24; G06F 30/20
  USPC ............................................................. 73/73
  See application file for complete search history.

(56) References Cited

FOREIGN PATENT DOCUMENTS

| CN | 103743655 | A |   | 4/2014 |           |
|----|-----------|---|---|--------|-----------|
| CN | 111047223 | A | * | 4/2020 |           |
| CN | 111047223 | A |   | 4/2020 |           |
| CN | 112162026 | A | * | 1/2021 | G01N 27/308 |
| CN | 112162026 | B |   | 7/2021 |           |
| CN | 114167031 | A |   | 3/2022 |           |
| CN | 114384023 | A | * | 4/2022 |           |
| CN | 114384023 | A |   | 4/2022 |           |

OTHER PUBLICATIONS

Translation of CN-114384023-A (Year: 2022).*
Translation of CN-112162026-A (Year: 2021).*
Translation of CN-111047223-A (Year: 2020).*
Search Report, prepared by Beijing Zhanqiao Intellectual Property Agency, dated Oct. 12, 2023.
(Continued)

*Primary Examiner* — Nathaniel T Woodward
(74) *Attorney, Agent, or Firm* — Zhu Lehnhoff LLP

(57) ABSTRACT

A model for predicting bioavailability of arsenic in site soil and a construction method and an application thereof, includes steps of: leveling soil after selecting a measuring point, vertically placing a measuring sleeve, fully supplying water to site soil to be measured, balancing for 20-40 min, measuring a water content in a soil volume not less than 40%, placing a piston DGT device into the measuring sleeve and pressing the device into soil, covering a top of the measuring sleeve with a wind shield, cleaning the piston DGT device after the measurement, analyzing a concentration of available arsenic by ICP-MS, and measuring available arsenic of soil; linearly fitting the available arsenic measured by a DGT method with human bioavailable arsenic measured by a UBM method, and obtaining a model for predicting bioavailability of arsenic in site soil.

9 Claims, 1 Drawing Sheet

(56) References Cited

OTHER PUBLICATIONS

Search Report, issued in CN202211382390.4 (priority application), by CNIPA, dated Oct. 9, 2023.
Notice of Grant of Patent Rights, issued in CN202211382390.4 (priority application), by CNIPA, dated Oct. 9, 2023.

* cited by examiner

MODEL FOR PREDICTING BIOAVAILABILITY OF ARSENIC IN SITE SOIL AND CONSTRUCTION METHOD AND APPLICATION THEREOF

REFERENCE TO RELATED APPLICATIONS

The present application claims the priority of Chinese patent application No. 202211382390.4, filed on 2022 Nov. 7, the entire disclose of which is incorporated herein by reference.

TECHNICAL FIELD

The present disclosure relates to the field of evaluating health risk of arsenic contaminated site soil, in particular to a method of evaluating health risk of arsenic contaminated site soil.

BACKGROUND

The traditional methods for evaluating bioavailability of heavy metals in soil have some limitations, such as complicated operation and great disturbance to samples. Usually, the occurrence forms of arsenic and other pollutants in soil will be changed due to the changes of environmental factors such as temperature, redox potential and so on during the collection, transportation and preservation of samples, which will further affect their bioavailability and make their analysis results have great errors. Compared with a traditional analytical technology, DGT technology is a pollutant in-situ measuring technology developed based on Fick's first diffusion law, which can enrich and quantify an ion passing through a diffusion layer with a specific thickness in a specific time, and can better reflect the process of absorption and enrichment of heavy metals by organisms, thus simulating a dynamic reaction process of soil more truly and effectively. The DGT technology has been widely used in evaluating the bioavailability of heavy metals in water, soil and sediments. DGT has the advantages of in-situ measurement, simple operation and high sensitivity in application. However, in the past, the application of the DGT technology mostly focused on the evaluation of plant availability in farmland soil and sediments, and the application of in-situ characterization in contaminated soil was less. This is mainly because the texture of farmland soil is relatively uniform, and the variability of soil physical and chemical properties is small, while the soil type and physical and chemical properties of the site are more complicated and the spatial variability is greater. At the same time, the spatial differences of physical and chemical properties of site soil (such as particle size, water content, temperature, salinity, organic matter content and other parameters) will also affect the accuracy and feasibility of in-situ measurement of available content of heavy metals in site soil by DGT. Therefore, the application of DGT in site soil is less, and its applicability and accuracy in in-situ measurement of the site need to be further verified. In addition, the research on the application of in-situ DGT in human health risk evaluation of site soil based on the bioavailability of heavy metals is still blank.

SUMMARY

The technical problem to be solved: the present disclosure provides a method of evaluating health risk of arsenic contaminated site soil, applies the method to the availableness-based site soil arsenic health risk evaluation, and guides the site to carry out the target value of green and sustainable remediation according to the calculated risk value.

Technical scheme: a method of constructing a model for predicting bioavailability of arsenic in site soil, including steps of: leveling soil after selecting a measuring point, vertically placing a measuring sleeve, fully supplying water to site soil to be measured, balancing for 20-40 min, measuring a water content in a soil volume not less than 40%, placing a piston DGT device into the measuring sleeve and pressing the device into soil, covering a top of the measuring sleeve with a wind shield, cleaning the piston DGT device after the measurement, analyzing a concentration of available arsenic by ICP-MS, and measuring available arsenic of soil; linearly fitting the available arsenic measured by a DGT method with human bioavailable arsenic measured by a UBM method, and obtaining a model for predicting bioavailability of arsenic in site soil: Log (As in an intestinal stage)=0.743 log (DGT-As)−0.598 Log $Al_o$+0.837, where $R^2$=0.852, P<0.001; wherein As in the intestinal stage is a content mg $kg^{-1}$ of As available to human body in the intestinal stage in soil measured by the UBM method; DGT-As is a concentration μg $L^{-1}$ of the available arsenic measured by the DGT device; $Al_o$ is a content g $kg^{-1}$ of active aluminum in soil.

Measuring time of the piston DGT device should be no less than 8 h, measuring temperature and time are recorded, and then a content of available arsenic in site soil is calculated.

Three DGT devices are placed at each measuring point.

A model for predicting bioavailability of arsenic in site soil generated by the construction method described above is provided.

Application of the prediction model described above in predicting availability of arsenic in site soil is provided.

Beneficial effect: the method solves the problems of complicated operation resulted from ectopic sampling analysis in the existing traditional site soil pollution evaluation, change of pollutant forms, over-estimation of risk values and over-repair of the site resulted from risk evaluation based on total amount. Taking the contaminated site list database established by the Canadian federal contaminated site action plan as an example, if the evaluation method based on bioavailability of heavy metals is used, the repair cost of all sites to be repaired in the federal contaminated site list can be reduced by 2 billion dollars. This will help to identify the harmful effects of heavy metals such as arsenic in site soil more efficiently and accurately, provide a more scientific basis for policy formulation and risk management, and provide technical support for guiding the green and sustainable remediation of arsenic-contaminated site soil, which has a good application prospect.

DETAILED DESCRIPTION OF THE EMBODIMENTS

Figure 1:
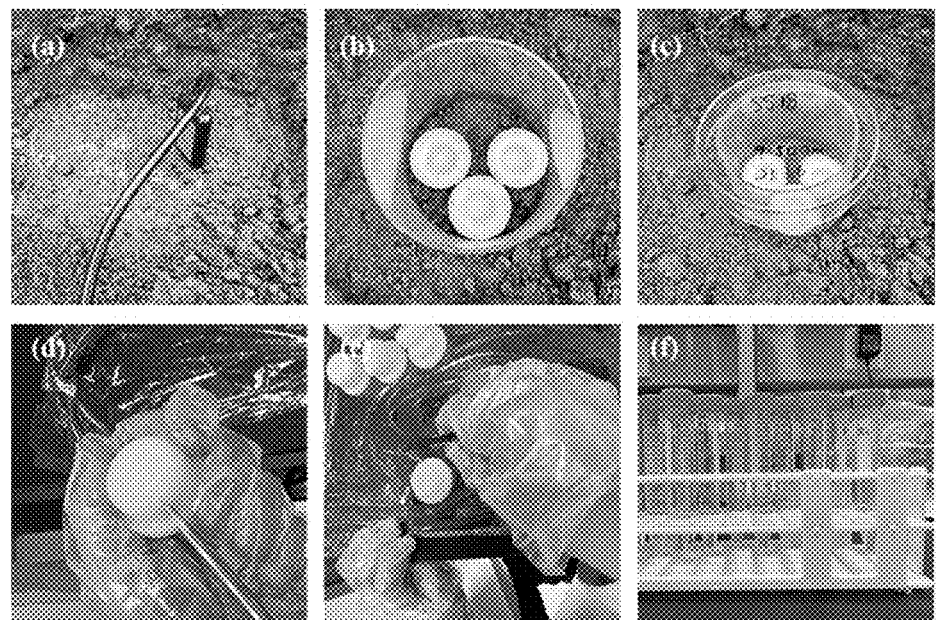
FIG. 1 is a flow chart of in-situ DGT measurement in the site, in which (a) the profile is leveled and water is added for balance; (b-c) in-situ DGT arrangement; (d-f) recovery and measurement of the DGT device.
Figure 2:
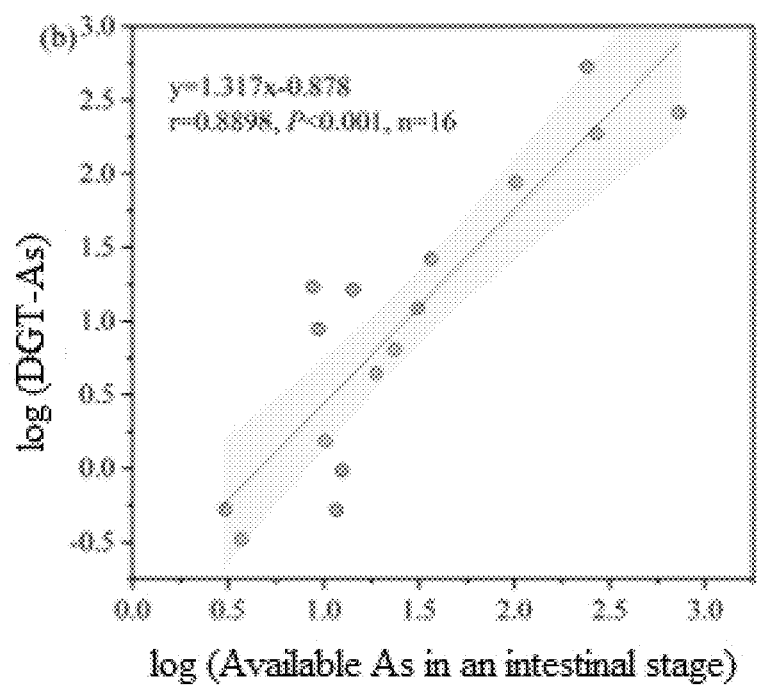
FIG. 2 shows a relationship between DGT extracted state As and human availability As in the gastrointestinal simulated intestinal stage in vitro.

Embodiment 1: the in-situ characterization technique of available arsenic of soil under suitable site conditions is established.

The in-situ characterization of available arsenic of soil by DGT is carried out in the relocation site of an iron and steel plant in Jiangsu Province, and the initial field adjustment of the relocation site is carried out by a grid layout method. On the basis of site investigation, four representative sites are selected to carry out in-situ characterization of available arsenic of soil under suitable site conditions. The soil in this site is weakly alkaline (pH: 8.14 to 8.48) with low organic matter content and sandy loam. The contents of total arsenic in the soil of the four survey sites are 59.8, 102.9, 90.9 and 73.9 mg kg$^{-1}$, respectively. Except for the site S1, the contents of As in the other sites all exceed the second-class land use risk screening value (60 mg kg$^{-1}$) in the Standard for Soil Pollution Risk Control of Construction Land for Soil Environmental Quality (GB 36600-2018), so that it is necessary to carry out further detailed pollution investigation and risk evaluation of As pollution in the site.

The in-situ DGT measuring method of the site is as follows: determining the sample area to be measured, levelling the soil, picking up larger gravel and plant roots in the soil, and dispersing and mixing the soil lumps as evenly as possible. After leveling the soil and determining the quadrat, a PVC pipe (a measuring sleeve) with a diameter of 10 cm and a height of 10 cm is vertically pressed into the site soil, and water is fully supplied to the soil to be measured. The soil moisture is measured with an in-situ hygrometer, and is kept balanced and stable for 30 min when the soil moisture is more than 40%. The DGT device is placed, and the top of the measuring sleeve is covered with a glass cover to reduce water evaporation. The DGT device is placed for measurement for more than 8 h under the condition that the soil moisture content is above 40%. After the measurement, the DGT device is taken out, the soil particles at the DGT window are immediately washed with distilled water, the DGT device are put into clean self-sealing bags and marked. The standing time and the soil temperature are recorded, and the DGT device is sent back to the laboratory for analysis. Three DGT devices are placed at each site as parallel samples. At the same time, the soil near the DGT device is collected for subsequent laboratory comparative analysis, a part of the soil is used to carry out DGT analysis in the laboratory and is compared with the site results, and the other part of the soil is used to measure the content of As in soil pore water.

The surface of the DGT device recovered from the site is washed with ultrapure water. After the DGT is turned on, the adsorption membrane is taken out and the adsorbed available arsenic is eluted. The concentration of available arsenic is analyzed by ICP-MS. The calculation method refers to the following formula:

the formula of calculating the concentration CDGT of available arsenic extracted by DGT:

$$C_{DGT} = \frac{M\Delta g}{DAt}$$

The target pollutant accumulation M in the fixed membrane is generally calculated by the following formula by solvent extraction:

$$M = \frac{C_e(V_e + V_g)}{f_e}$$

where $C_e$ is the concentration of the extracting solution; $V_e$ is the volume of the extracting solution; V g is the volume of the fixed membrane; $f_e$ is the extraction rate of the extracting solution of target ions on the fixed membrane.

where t is the measuring time s of the DGT device; M is the accumulation μg of target pollutants of the fixed membrane in the time period measured by the DGT device; A is the area cm$^2$ of an exposed window of the DGT device; Δg is the thickness cm of a diffusion layer (including a filter membrane and a diffusion membrane); D is the diffusion coefficient cm$^2$ s$^{-1}$ of the substance to be measured; CDGT is the average concentration μg L$^{-1}$ of the substance to be measured in a certain period of time; $C_e$ is the concentration μg L$^{-1}$ of the extractive solution; $V_e$ is the volume mL of the extracting solution; V g is the volume mL of the fixed membrane; $f_e$ is the extraction rate of the extracting solution of target ions on the fixed membrane.

Taking point 1 as an example, the concentration CDGT of the available arsenic extracted by DGT is calculated.

The DGT device that has been placed at point 1 of the site soil for not less than 8 h is recovered. Three parallel samples are provided at each point, and are brought back to the laboratory to elute the available arsenic adsorbed by the fixed membrane with 0.5 mol L$^{-1}$ NaOH solution. The arsenic concentration $C_e$ is measured in the extracting solution by the ICP-MS as 2.54, 2.29 and 2.06 μg L$^{-1}$, respectively. The eluent volume $V_e$ is 10 mL, the fixed membrane volume $V_g$ is 0.15 mL, the extraction rate $f_e$ of arsenic by the eluent is 100%, and the accumulated M of arsenic in the fixed membrane is 25.8, 23.2 and 20.9 ng, respectively, after being substituted into the formula. The thickness Δg of the diffusion layer in the DGT device is 0.078 cm. The average temperature during the measurement of the DGT device is recorded as 25° C., and the diffusion coefficient of arsenic is 5.38×10$^{-6}$ cm$^2$ s$^{-1}$ at this time. The area A of the exposed window of the DGT device is 2.54 cm$^2$. The standing time of the DGT device is 86400 s. The concentration of CDGT is 1.82±0.19 μg L$^{-1}$ after being substituted into the formula.

Embodiment 2: a model for predicting bioavailability of arsenic in site based on the in-situ DGT technology is established.

In vitro test can effectively reproduce the release behavior and toxicological effects of heavy metals in human digestive tract after oral intake by simulating the composition and digestion process of gastrointestinal fluids with different ratios. The evaluation method of bioavailability of heavy metals represented by the UBM method can effectively evaluate the human availability of heavy metals in soil, and has been widely used in evaluating the health risks of heavy metals in recent years. According to the previous work on the availability of arsenic in different sites, the available arsenic measured by the DGT method is linearly fit with human bioavailable arsenic measured in the gastric stage and the intestinal stage by the UBM method. Through stepwise multiple linear regression analysis and significant difference test of logarithms of human gastrointestinal simulated bioavailable arsenic, DGT extracted arsenic and soil physical and chemical properties measured by the UBM method, the variables that have no significant influence on the goodness of fit of the equation statistically are excluded from the prediction model. A model for predicting bioavailability of arsenic in site soil based on in-situ DGT technology is established.

Because the intestine is the main place for human absorption, considering the actual human absorption, a model for predicting bioavailability of arsenic through oral intake and exposure is established, and the site health risk evaluation based on DGT technology is carried out.

| The equation of the prediction model is as follows: | | |
|---|---|---|
| prediction model | $R^2$ | P |
| Log (As in the intestinal stage) = 0.743 Log (DGT-As) − 0.598 Log $Al_o$ + 0.837 | 0.852 | <0.001 |

In the equation, the data are logarithmically transformed to obtain normal distribution data satisfying the modeling requirements. As in the intestinal stage is the content mg $kg^{-1}$ of As available to human body in the intestinal stage in soil measured by the UBM method; DGT-As is a concentration µg $L^{-1}$ of the available arsenic measured by the DGT device; $Al_o$ is the content g $kg^{-1}$ of active aluminum in soil.

The value of available arsenic measured by the in-situ DGT is brought into the prediction model to obtain the content of bioavailability arsenic in the site soil, so as to evaluate the soil health risk and calculate the health risk value of arsenic in the site soil.

Taking point S2 of the relocation site of an iron and steel plant in Jiangsu Province as an example, the content of DGT extracted arsenic measured by the DGT technology is used to predict the content of bioavailability arsenic in the site soil. The total arsenic content in the soil at point S2 is 102.9 mg $kg^{-1}$, and the concentration CDGT of available arsenic extracted by DGT is 16.3 µg $L^{-1}$, and the content of active aluminum $Al_o$ in the soil is 4.1 g $kg^{-1}$. The content of arsenic available to human body in the intestinal stage in soil obtained by the prediction model is 23.5 mg $kg^{-1}$, which is not much different from the content 24.2 mg $kg^{-1}$ of available arsenic measured by the UBM method, and meets the prediction requirements of the model. Furthermore, in the Technical Guidelines for Risk Evaluation of Soil Pollution in Construction Land (HJ 25.3-2019), the human health risks of arsenic through oral intake of soil, skin contact with soil and inhalation of soil particles for exposure are evaluated. According to the risk evaluation model in the guidelines, when the carcinogenic risk CR of the contaminated site exceeds $1\times10^{-6}$ or the non-carcinogenic hazard quotient HQ exceeds 1, it indicates that the site has unacceptable risks and should be repaired according to the actual situation of the site. The total carcinogenic risk TCR calculated according to the total arsenic content in soil is $9.8\times10^{-5}$, and the total carcinogenic risk TCR calculated based on availableness is $2.2\times10^{-5}$. The total non-carcinogenic hazard quotient THQ calculated according to the total arsenic content in soil is 1.49, and the non-carcinogenic hazard quotient THQ calculated based on availableness is 0.34. The results show that the TCR of the evaluation result is greatly reduced by introducing the availableness prediction model, and the result still exceeds the acceptable cancer risk level, but the THQ at this point is reduced from 1.49 to 0.34, which is at an acceptable level. The model of predicting bioavailability of site arsenic based on the in-situ DGT technology established by this technology considers the availability of heavy metals in soil, and can identify the harmful effects of heavy metals in the site more accurately, which can provide a more scientific basis for policy formulation and risk management. In this way, the remediation target of the site can be calculated more conveniently and objectively according to the risk control value, which is helpful to guide the soil remediation industry in China to develop in a green and sustainable direction.

The above-mentioned embodiments are only preferred embodiments for better explaining the present disclosure. Therefore, the above-mentioned embodiments are not used to limit the present disclosure. Modifications, improvements and substitutions made within the principle of the present disclosure should be included in the scope of protection of the present disclosure.

What is claimed is:

1. A method of constructing a model for predicting bioavailability of arsenic in site soil, comprising steps of: leveling soil after selecting a measuring point, vertically placing a measuring sleeve, fully supplying water to site soil to be measured, balancing for 20-40 min, measuring a water content in a soil volume not less than 40%, placing a piston DGT device into the measuring sleeve and pressing the device into soil, covering a top of the measuring sleeve with a wind shield, cleaning the piston DGT device after the measurement, analyzing a concentration of available arsenic by ICP-MS, and measuring available arsenic of soil; linearly fitting the available arsenic measured by a DGT method with human bioavailable arsenic measured by a UBM method, and obtaining a model for predicting bioavailability of arsenic in site soil: Log (As in an intestinal stage)=0.743 log (DGT-As)−0.598 Log $Al_o$+0.837, where $R^2$=0.852, P<0.001; wherein As in the intestinal stage is a content mg $kg^{-1}$ of As available to human body in the intestinal stage in soil measured by the UBM method; DGT-As is a concentration µg $L^{-1}$ of the available arsenic measured by the DGT device; $Al_o$ is a content g $kg^{-1}$ of active aluminum in soil.

2. The method of constructing the model for predicting bioavailability of arsenic in site soil according to claim 1, wherein measuring time of the piston DGT device should be no less than 8 h, measuring temperature and time are recorded, and then a content of available arsenic in site soil is calculated.

3. A model for predicting bioavailability of arsenic in site soil generated by the construction method according to claim 2.

4. Application of the prediction model according to claim 3 in predicting availability of arsenic in site soil.

5. The method of constructing the model for predicting bioavailability of arsenic in site soil according to claim 1, wherein three DGT devices are placed at each measuring point.

6. A model for predicting bioavailability of arsenic in site soil generated by the construction method according to claim 5.

7. Application of the prediction model according to claim 6 in predicting availability of arsenic in site soil.

8. A model for predicting bioavailability of arsenic in site soil generated by the construction method according to claim 1.

9. Application of the prediction model according to claim 8 in predicting availability of arsenic in site soil.

* * * * *